United States Patent [19]

LaMattina et al.

[11] 4,443,621

[45] Apr. 17, 1984

[54] P-NITROPHENYL 3-BROMO-2,2-DIETHOXY-PROPIONATE AND SYNTHETIC UTILITY THEREFOR

[75] Inventors: John L. LaMattina, Ledyard; Paul D. Weeks, Gales Ferry, both of Conn.

[73] Assignee: Pfizer Inc., New York, N.Y.

[21] Appl. No.: 474,958

[22] Filed: Mar. 14, 1983

[51] Int. Cl.$^3$ .................. C07C 79/12; C07D 309/40
[52] U.S. Cl. ................................ 560/142; 549/418
[58] Field of Search .................................. 560/142

[56] References Cited

U.S. PATENT DOCUMENTS

| | | |
|---|---|---|
| 3,130,204 | 4/1964 | Tate et al. ........................ 549/418 |
| 3,365,469 | 1/1968 | Tate et al. ........................ 549/418 |
| 3,468,915 | 9/1969 | Tate ................................. 549/418 |
| 3,644,635 | 2/1972 | Tate et al. ........................ 424/283 |
| 4,082,717 | 4/1978 | Brennan et al. .................. 549/418 |
| 4,282,151 | 8/1981 | Batz et al. ........................ 560/142 |

*Primary Examiner*—Glennon H. Hollrah
*Assistant Examiner*—Patricia M. Scott
*Attorney, Agent, or Firm*—Charles J. Knuth; Albert E. Frost; Robert K. Blackwood

[57] ABSTRACT p-Nitrophenyl 3-bromo-2,2-diethoxypropionate, useful in the synthesis of highly functionalized small molecules and heterocycles, including pyromeconic acid and 6-methylpyromeconic acid.

1 Claim, No Drawings

P-NITROPHENYL 3-BROMO-2,2-DIETHOXY-PROPIONATE AND SYNTHETIC UTILITY THEREFOR

BACKGROUND OF THE INVENTION

The present invention is concerned with p-nitrophenyl 3-bromo-2,2-diethoxypropionate, of the formula

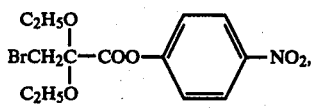

useful in the synthesis of highly functionalized small molecules and heterocycles, particularly pyromeconic acid (2) and 6-methylpyromeconic acid (3).

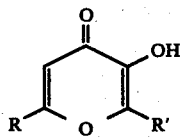

(2) R=R'=H
(3) R=CH$_3$, R'=H
(4) R=H, R'=CH$_3$
(5) R=R'=CH$_3$

Pyromeconic acid and 6-methylpyromeconic acid have particular value in the synthesis of maltol (4, Tate et al., U.S. Pat. No. 3,130,204) and 6-methylmaltol (5, Tate, U.S. Pat. No. 3,468,915), respectively, as well as other valuable 2-substituted pyromeconic acid derivatives (for example, see Tate et al., U.S. Pat. Nos. 3,365,469 and 3,644,635; Brennan et al., U.S. Pat. No. 4,082,717), which are useful in enhancing flavors or aromas, and/or in the inhibition of bacteria or fungi.

SUMMARY OF THE INVENTION

Highly functionalized small molecules that can be chemoselectively manipulated are of great value to the synthetic organic chemist. Of particular interest would be a derivative of a 3-halopyruvic acid in which the acid moiety is activated toward nucleophilic attack. Such a molecule would consist of an alpha-haloketone linked directly to an activated carboxylic acid, and would contain, in effect, three contiguous electro-positive carbon atoms. Clearly, chemoselectivity in the reactions of such a molecule with nucleophiles would be difficult to realize, unless a molecule can be found in which each carbon atom can be differentiated. Furthermore, for a synthon of this type to be of general utility, it should be readily available on large scale, and be reasonably stable. We have now discovered a reagent which meets these criteria, viz., p-nitrophenyl 3-bromo-2,2-diethoxypropionate (NPBDP, 1). NPBDP possesses an alpha-bromoketone moiety masked as a ketal, along with an active carboxylic ester. It is readily prepared in large quantities by ketalization of commercially available alpha-bromopyruvic acid, followed by reaction with p-nitrophenyl trifluoroacetate. NPBDP is a crystalline solid of mp 75°–76° C., which can be stored routinely for over a year without decomposition. This work further describes the utility of (1) in the synthesis of highly functionalized small molecules, as well as heterocycles, in particular pyromeconic acid and 6-methylpyromeconic acid.

The present invention should not be so narrowly construed as to be limited to p-nitrophenyl 3-bromo-2,2-diethoxypropionate per se, since numerous equivalent compounds will be obvious to those skilled in the art. Such compounds include, for example, those in which the C-2 ketal group is replaced by one derived from an alternative alcohol, or from a diol; those in which the C-3 bromo group is replaced by an alternative leaving group (i.e., a group subject to similar nucleophilic displacement); and those in which the C-1 p-nitrophenyl group is replaced by a group of similar reactivity.

DETAILED DESCRIPTION OF THE INVENTION

The valuable, new synthetic reagent of the present invention (NPBDP, 1) is readily prepared in large quantities and in high yield from commercially available alpha-bromopyruvic acid.

The ketone group of the bromopyruvic acid is first converted to the ketal, by reaction of that ketoacid with at least two equivalents of ethanol, usually employing a large excess of ethanol which further serves as solvent for the reaction, under substantially anhydrous conditions, in the presence of a strong acid catalyst, e.g. HCl, H$_2$SO$_4$ or an organic sulfonic acid. Alternatively and preferably, the ketal is formed by reacting the bromopyruvic acid with ethyl orthoformate, also usually in excess and serving as the reaction solvent, again in the presence of a strong acid catalyst, preferably sulfuric acid. In either process, temperature is not critical, for example, 0°–50° C. being satisfactory. Since energy costs associated with heating or cooling are avoided, ambient temperature (usually in the range of about 16°–28° C.) is preferred.

In the second stage, the intermediate 3-bromo-2,2-diethoxypropionic acid is reacted with substantially one equivalent of p-nitrophenyl trifluoroacetate, in the presence of at least one equivalent of a tertiary amine, usually in excess. The preferred amine is pyridine, used in sufficient excess to further serve as solvent for the reaction. Temperature is not critical, e.g., 0°–50° C. is satisfactory. For reasons stated above, ambient temperature is preferred.

Although NPBDP contains two potential sites for nucleophilic attack, and both sites have structure suggesting them to be sterically hindered, a wide variety of nucleophiles react readily and exclusively at the active ester. For example, ammonia and acetamide oxime react smoothly with NPBDP to give 3-bromo-2,2-diethoxypropionamide and the corresponding acetamidino ester derivative, respectively. Reaction of NPBDP with the sodium salt of dimethyl malonate affords dimethyl 2-(3-bromo-2,2-diethoxypropionyl)malonate. Even a potent nucleophile such as alphalithioacetonitrile reacts chemoselectively with NPBDP to afford 5-bromo-4,4-diethoxy-3-oxovaleronitrile.

Even though the alpha-bromoketal is inert to intermolecular reaction, intramolecular reactions can occur when bifunctional nucleophiles are employed. Such synthetic utility of NPBDP (1) is illustrated by its use in the synthesis of valuable pyromeconic acid and 6-methylpyromeconic acid:

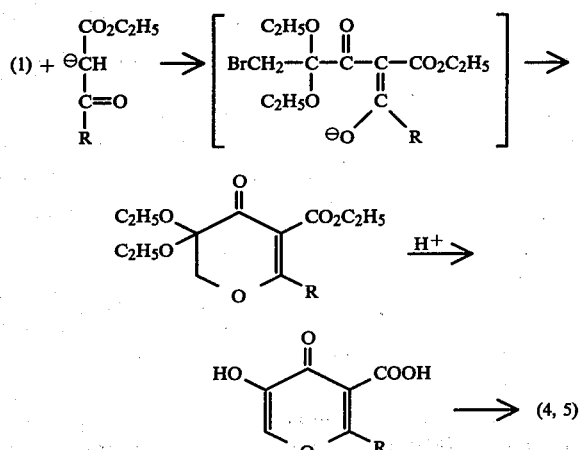

(6) R=CH₃
(7) R=H
(8) R=CH₃
(9) R=H as exemplified below.

Heterocyclic molecules are also derived from the above polyfunctional small molecules, which behave similarly. For example, 5-bromo-4,4-diethoxy-3-oxovaleronitrile is reacted with hydrazine, forming (via hydrazone formation, cyclization and ethanol elimination) 3-cyanomethyl-4-ethoxypyrazole; and acetimido 3-bromo-2,2-diethoxypropionate is cyclized on warming to produce 3-methyl-5-(2-bromo-1,1-diethoxyethyl)-1,2,5-oxadiazole. The latter is deketalized by warming in 95% formic acid to produce the corresponding 3-methyl-5-(2-bromoacetyl)-1,2,5-oxadiazole.

The present invention is illustrated by the following Examples. However, it should be understood that the invention is not limited to the specific details of these Examples.

EXAMPLE 1

3-Bromo-2,2-diethoxypropionate Acid alpha-Bromopyruvic acid (100 g, 0.60 mole), 240 mL triethyl orthoformate and H₂SO₄ (4 mL) were combined and the resulting solution stirred 24 hours, then diluted with 1.2 L CH₂Cl₂. The organic phase was separated, washed 2×100 mL H₂O and then 1×100 mL saturated NaCl, dried over Na₂SO₄, evaporated and dried in vacuo 4 hours to yield title product as a white solid, 144 g (99%); mp 80°–85° C. This product was of sufficient purity for direct use in the next step. A sample recrystallized from cyclohexane gave mp 91°–92° C.

EXAMPLE 2 p-Nitrophenyl 3-Bromo-2,2-diethoxypropionate (NPBDP 1)

Title product of the preceding Example (144 g, 0.60 mole), p-nitrophenyl trifluoroacetate (141 g; 0.60 mole), and pyridine (405 mL) were stirred under N₂ for 24 hours, then poured into 2 L H₂O and extracted 4×500 mL ether. The extracts were combined, washed 5×175 mL 5% NaOH, dried over Na₂SO₄, and evaporated to an oil which crystallized on scratching. Recrystallization from hexane gave purified title product as a stable, white crystalline solid; 169 g (77%), mp 75°–76° C.

EXAMPLE 3

Ethyl 2,3-Dihydro-3,3-diethoxy-6-methyl-4-pyrone-5-carboxylate (6)

Under N₂, NaH (1.06 g, 44 mmole) was stirred in 100 mL dry tetrahydrofuran (THF). A solution of ethyl acetoacetate (5.47 g, 42 mmole) in 20 mL of dry THF was added dropwise over 15 minutes, followed by NPBDP (7.24 g, 20 mmole) in 80 mL dry THF over 5 minutes. The resulting mixture was refluxed for 4 hours, cooled, poured into 400 mL ice water, adjusted to pH 7 with 1 N HBr, and extracted 3×80 mL CHCl₃. The extracts were combined, dried over Na₂SO₄ and evaporated to an oil. The oil was chromatographed on 260 g silica gel, using isopropyl ether as eluant. Following elution of less polar ethyl acetoacetate and p-nitrophenol, title product eluted as an oil which distilled in vacuo to yield purified title product; 3.46 g (63%); bp 110°–115° C./0.2 mm.

Anal. Calcd. for C₁₃H₂₀O₆: C, 57.34; H, 7.40; Found: C, 57.12; H, 7.28.

Substituting an equivalent amount of ethyl formylacetate for ethyl acetoacetate yields ethyl 2,3-dihydro-3,3-diethoxy-4-pyrone-5-carboxylate (7).

EXAMPLE 4

2-Methyl-5-hydroxy-4-pyrone-3-carboxylic Acid (8)

Under nitrogen, a solution of title product of the preceding Example (3.46 g) is heated in 95% formic acid at 85° C. for 1 hour. The mixture is cooled and evaporated in vacuo to yield present title product.

In like manner, compound (7) of the preceding Example is converted to 5-hydroxy-4-pyrone-3-carboxylic acid (9).

EXAMPLE 5

6-Methylpyromeconic Acid (4)

Title product of the preceding Example (3.0 g, 0.012 mole) is stirred with 12 mL of dimethyl phthalate and heated to 220°–240° C. until evolution of carbon dioxide is complete (about 15 minutes). The mixture is cooled to about 80° C. and fractionally distilled in vacuum at 1–10 mm. Title product is found in fractions distilling below the boiling point of dimethyl phthalate, which is 148° C./10 mm, 132°/5 mm and 100° C./1 mm.

In the same manner, compound (9) of the preceding Example is converted to pyromeconic acid.

We claim:
1. p-Nitrophenyl 3-bromo-2,2-diethoxypropionate.

* * * * *